(12) United States Patent
Shulov et al.

(10) Patent No.: US 7,208,150 B1
(45) Date of Patent: Apr. 24, 2007

(54) ANALGESIC FROM SNAKE VENOM

(75) Inventors: Aharon Shulov, deceased, late of Jerusalem (IL); by Shlomit Shulov Barkan, legal representative, Mevaseret Zion (IL); Naftali Primor, Jerusalem (IL)

(73) Assignee: S.I.S. Shulov Institute for Science Ltd., Rehovot (IL)

( * ) Notice: Subject to any disclaimer, the term of this patent is extended or adjusted under 35 U.S.C. 154(b) by 0 days.

(21) Appl. No.: 10/030,380

(22) PCT Filed: Jul. 14, 1999

(86) PCT No.: PCT/IL99/00386

§ 371 (c)(1),
(2), (4) Date: Jul. 25, 2002

(87) PCT Pub. No.: WO01/03710

PCT Pub. Date: Jan. 18, 2001

(51) Int. Cl.
*A61K 38/46* (2006.01)
*A61K 39/395* (2006.01)
*C07K 16/00* (2006.01)

(52) U.S. Cl. .................. 424/94.67; 424/172.1; 530/387.1

(58) Field of Classification Search ........ 424/742, 424/94.67, 172.1; 530/387.1
See application file for complete search history.

(56) References Cited

U.S. PATENT DOCUMENTS 4,162,303 A * 7/1979 Sanders .................. 435/5

6,057,297 A * 5/2000 Politi et al. .................. 514/19

FOREIGN PATENT DOCUMENTS

| CN | 1072344 | 5/1993 |
|---|---|---|
| EP | 0246861 | 11/1987 |
| SU | 435824 | 6/1975 |
| WO | WO 91/01740 | 2/1991 |
| WO | WO 99/36078 | 7/1999 |

OTHER PUBLICATIONS

Mancin et al. "The analgesic activity of crotamine, a neurotoxin from *Crotalus durissus terrificus* (South American rattlesnake) venom: A biochemical and pharmacological study." *Toxicon*, vol. 36, No. 12, Dec. 1998 : 1927-1937.
Giorgi, R. Bernardi, M.M. and Cury, Y. (1993) *Toxicon* 31:1257-1265.
Bevan, P. And Hiestand, P. (1983) *J. Biol. Chem.* 258:5319-5326.
Dutta, A.S. and Chaudhuri, A.K.N. (1991) *Indian J. Exp. Biol.* 29:937-942.
Pu, X.C. Wong, P.T.H. and Gopalakrishnakone, p. (1995) *Toxicon* 33:1425-1431.

* cited by examiner

*Primary Examiner*—Susan Hoffman
*Assistant Examiner*—Randall Winston
(74) *Attorney, Agent, or Firm*—The Nath Law Group; Gary M. Nath; Susanne M. Hopkins

(57) ABSTRACT

A substantially non-toxic fraction isolated from snake venom is disclosed, which fraction has an analgesic effect. The fraction has the characteristics of a fraction from snake venom purified on a Mono Q ion exchange column. Also described are a pharmaceutical composition for use as an analgesic comprising the non-toxic fraction, and a method for the relief of pain comprising administrating the non-toxic fraction.

14 Claims, 6 Drawing Sheets

ANALGESIC FROM SNAKE VENOM

FIELD OF THE INVENTION

The present invention relates to the use of snake venom as an analgesic.

BACKGROUND OF THE INVENTION

Although pain is a crucially important physiological response, it also results in unnecessary suffering and agony. The control and relief of pain is an important branch of medicine. Pain may come about both as a result of disease as well as a result of medical treatment such as chemotherapy. In either case, it is important to alleviate the pain as much as possible so as to enable the sufferer to function normally.

Two neural pathways relating to pain act concurrently in the body: (1) a sensory pathway which senses tissue damage and subsequently produces a feeling of pain; (2) an analgesic pathway which reduces the feeling of pain and prevents the flow of information about the pain to the central nervous system (CNS), thus allowing the organism to maintain it's normal activity in spite of an injury. Anesthesia can be realized either by use of a drug which inhibits peripheral nerves that act as pain sensors or by enhancement of the natural analgesic system. Since these are different pathways, they are affected by different substances. For example, aspirin and lidocaine are active on the peripheral sensory pathway, while morphine and related substances are active on the analgesic system.

The most efficient analgesics currently in use are morphine-related substances of opiatic origin. It's well known that the brain makes a variety of endogenic opiates, and this explains the powerful effect of these substances. Their action on neurons is mediated by specialized receptors. Signals regulated by these receptors prevent the flow of information from the peripheral pain neurons to the CNS. These CNS neurons are also sensitive to a variety of other chemical substances including catecholamines (serotonin, noradrenalin etc.), neuroactive peptides (neurotensin) and inhibitory amino acids (glycin and GABA).

Out of some 4000 currently living species of snakes, approximately 400 species are known to be venomous. The venomous species are classified into five families, being Viperidae, Elapidae, Crotolidae, Hydrophidae and Atractaspidae. Snakes of the Viperidae family are distributed in Europe, Asia and Africa, and comprise 8 genera, one of which is the genus Vipera The Crotolidae family includes the genus *Crotalus*. The Elapidae family includes the genus *Naja*.

Snake venom comprises a large variety of different substances. Out of several hundreds of estimated compounds, it is believed that only 4–8 are involved in the toxic effect of the venom. Despite functional similarity, snake venoms differ considerably in their chemical composition. Each species possesses its own characteristic venom composition. To date, only a few hundred compounds from some 400 venomous snake species have been characterized. These include enzymes, toxins, growth factors, etc. Most of the isolated venom compounds are of unknown function.

Traditionally, snake venom is considered a source of toxic substances. However, it is also a source of analgesics. Doctors who treated patients bitten by a South American snake (*Crotalus durissus terrificus*) reported that although these patients were in a life-threatening condition, they felt no pain. A neurotoxin product isolated from snake venom was regarded as a new type of analgesic at the First Congress of Neurotoxicology (1977) in Yugoslavia. These and other observations led to attempts to isolate anesthetic compounds from snake venom.

Bevan, P. and Hiestand, P. (1983) *J Biol Chem.* 258: 5319–5326 describe a single chain polypeptide isolated from *Vipera russelli russelli* venom by cation exchange chromatography. The polypeptide competes with the binding of monoamines and opiate ligands to their respective receptors, and injection of the polypeptide intracerebroventricularly in rats causes marked sedation. The authors state that the polypeptide is a large and highly charged molecule which is unlikely to pass the blood-brain barrier. The polypeptide was found to be a moderately potent toxin, similar to the crude venom.

Dutta, A. S. and Chaudhuri, A. K. N. (1991) *Indian J Exp. Biol* 29:937–942 describe experiments carried out with crude venom of *Vipera ruselli* on mice and rats. The venom was injected intraperitoneally and intravenously, and was found to produce alterations in general behavior patterns connected with the CNS The venom showed significant analgesic activity in one assay, but no activity in two other assays.

WO 91/01740 published Feb. 21, 1991 discloses the use of lyophilized *Crotalus atrox* whole venom in a pharmaceutical composition for external use. The composition has analgesic, hyperaemizating and spasmolysant activity.

Giorgi, R., Bernardi, M. M. and Cury, Y. (1993) *Toxicon* 31:1257–1265 describe analgesic effects evoked by low molecular weight substances extracted from *Crotalus durissus terrificus* venom by ultrafiltration. The extract was administered to mice subcutaneously, intraperitoneally and orally.

CN 1,072,344 published May 26, 1993 discloses a snake toxin ointment containing a commercial snake toxin enzyme (source not given), a leukocyte peptide factor and Bingpian, a known Chinese analgesic medicine. The ointment functions as an antibiotic with no toxicity or side effects.

Pu, X. C., Wong, P. T. H. and Gopalakrishnakone, P. (1995) *Toxicon* 33:1425–1431 describes a neurotoxin purified from king cobra venom by gel filtration and HPLC. The toxin was administered i.p., p.o. or i.c.v. to mice and found to have a potent analgesic effect.

U.S.S.R. Patent No. 435,824 describes an analgesic composition prepared from Nayaksin dry cobra venom. This snake is from the *Naja* species which belongs to the Elapidae family.

For over 20 years, an ointment named Viprosalum or Viprosal has been available in the former Soviet Union and in Eastern Europe for the relief of pain. This ointment is a mixture of a viper venom (European species) dissolved in Vaseline together with Lanolin, camphor and solicilate.

SUMMARY OF THE INVENTION

It is an object of the present invention to provide an analgesic substance isolated from snake venom which is substantially non-toxic.

According to one aspect of the present invention, there is provided a substantially non-toxic fraction isolated from snake venom having the characteristics of a fraction purified from the venom by Mono Q ion-exchange chromatography, wherein the fraction has an analgesic effect.

In a preferred embodiment of this aspect of the invention, the chromatography is carried out on a Mono Q column in 20 mM Tris-HCl buffer pH 7.0, and the fraction elutes at 12–28 minutes. It should be emphasized that the above conditions are intended to define the fraction of the invention, and not to limit the manner in which the fraction may be prepared. In other words, the fraction of the invention may be prepared from snake venom by a variety of purification methods. However, it is defined as having the characteristics of a fraction purified as defined above.

Further in accordance with this aspect of the present invention, there is provided a pharmaceutical composition for use as an analgesic comprising a substantially non-toxic fraction isolated from snake venom having the characteristics of a fraction purified from the venom by Mono Q ion-exchange chromatography, wherein the fraction has an analgesic effect.

In a preferred embodiment of the present invention, the pharmaceutical composition is for topical use.

In a further aspect of the invention, there is provided a method for isolating a substantially non-toxic fraction from snake venom which has an analgesic effect, the fraction being purified from the venom by ion-exchange chromatography using an aqueous buffer.

In a preferred embodiment of this aspect of the invention, the ion-exchange chromatography is by a Mono Q FPLC column. In a further preferred embodiment, the aqueous buffer is Tris-HCl buffer or ammonium acetate buffer. In a particularly preferred embodiment, the concentration of the buffer is 20 mM and the pH is in the range of 6.8–7.5.

The fraction provided by the invention combines a number of properties previously unreported as appearing together in the same material. These properties include: (1) possession of analgesic activity; (2) substantially no toxicity; and (3) substantially purified.

In the present specification, the term non-toxic is defined as the non-occurrence of pathological phenomena as a result of using pharmacological levels of the fraction of the invention which have an analgesic effect The term substantially non-toxic is defined as including acceptably low toxicity as well as non-toxicity.

The fraction of the invention may be isolated from a variety of venomous snakes from the families Viperidae, Elapidae, Crotolidae, Hydrophidae and Atractaspidae. Although experiments described below which illustrate the invention involve the snake species *Vipera xanthina, Vipera russelli, Crotalus adamanteus* and *Naja melanoleuca*, it is to be understood that these species serve only as examples for the five families of venomous snakes listed above.

Although the fraction of the invention is a purified fraction of the crude venom, it apparently comprises more than one substance. The present invention includes not only the fraction of the invention but also various products which may be purified from the fraction of the invention and which possess the properties of the fraction of the invention. The invention also includes derivatives of these products, which retain the properties of the fraction of the invention. In the case of proteinaceous material, such derivatives would include proteins or polypeptides in which one or more amino acids have been added, deleted and/or replaced. Other chemical modifications are also contemplated.

The fraction of the invention may be used to prepare a pharmaceutical composition for use as an analgesic. Such a composition would also comprise a pharmaceutically acceptable carrier or excipient such as a mixture of Lanolin and Vaseline. The composition may be prepared for parenteral use, for example in a saline solution, or for topical use in an ointment, cream or salve. In order to afford relief to a subject suffering from pain, the pharmaceutical composition would either be injected or applied topically at an appropriate location. Other possible modes of application would be oral and rectal. Any pharmaceutical composition would generally include a pharmaceutically acceptable carrier or excipient in addition to the active ingredient. As the fraction of the invention sometimes acts after a lag period, it is to be expected that it will be especially effective with respect to chronic pain, although it may be used to treat any type of pain.

BRIEF DESCRIPTION OF THE DRAWINGS

The present invention will be better understood from the following detailed description of preferred embodiments, taken in conjunction with the following drawings in which:

FIG. 5 illustrates the results obtained during a purification of *Naja melanoleuca* venom on a Mono Q column using Tris-HCl buffer; and.

DETAILED DESCRIPTION OF PREFERRED EMBODIMENTS

Materials and Methods

Venoms

Figure 1A:
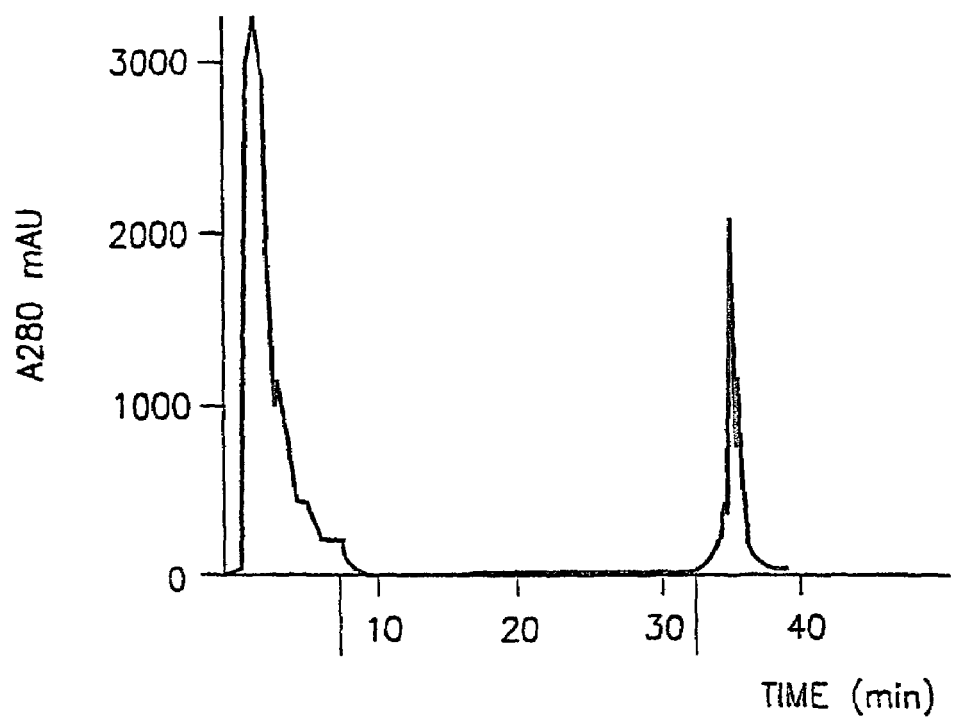
FIGS. 1A and 1B are graphs illustrating the results obtained during purification of *Vipera palestinae* venom on a Mono Q column. The Y-axis represents the UV absorbency at 280 nm and the X-axis is the elution time in minutes. Graph B is an enlargement of graph A in the region of 9–31 minutes, and at a lower range of absorbencies.
Figure 1B:
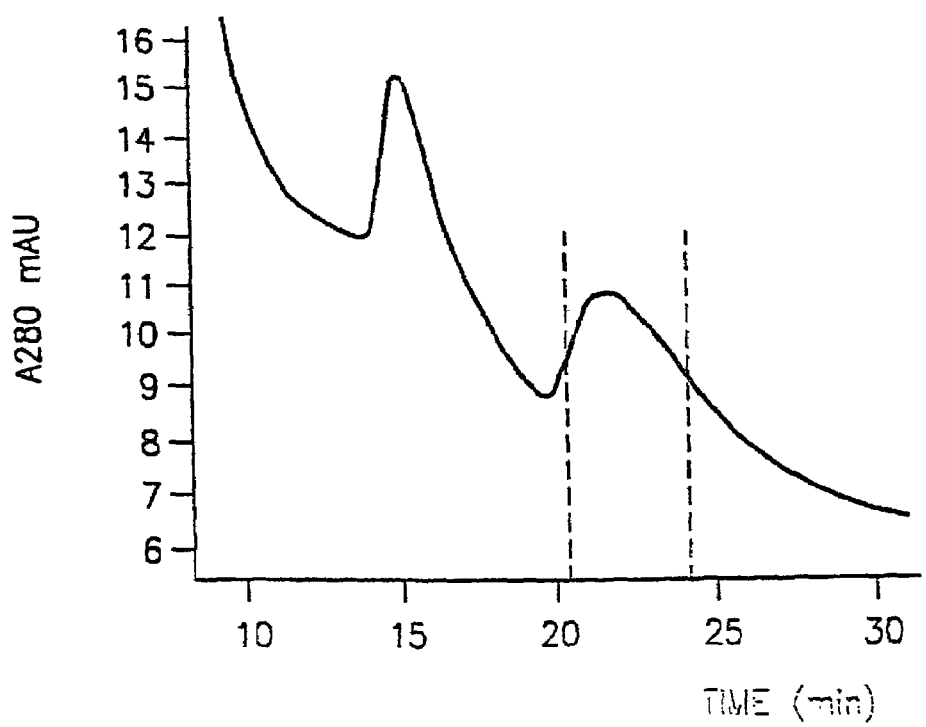

*Vipera palestinae* venom was obtained by milking several hundred snakes. Their venom was frozen and lyophilized. Other *Vipera* venoms were purchased from 'Latoxin', Rosans, France. *Crotalus adamanteus* and *Naja melanoleuca* venoms were purchased from 'Quality Venoms for Medical Research', New York, U.S.

Assays

A. Analgesic Assay

In each test, a few tens of hamsters of similar weight and age were used. The hamsters were divided into groups according to the number of samples to be tested. Ointment (50% Lanolin and 50% Vaseline) containing the tested substance was applied to the animal's fur on the back region. The fur was not removed so as to ensure that no damage to the skin occurred A control group of hamsters was treated with ointment without the fraction of the invention. Hamsters were treated by topical application for 6, 14 or 21 consecutive days. The test for analgesity was conducted on the day following the last application of the ointment.

In a typical test, a constant amount of ointment with or without an analgesic substance is applied to each animal for a predetermined period of days. Following this period, pain is induced by a subcutaneous injection of 0.8 ml of 1N HCl/0.1 kg body weight in the femur region. The hamsters respond to the HCl injection by touching the area of injection with the tongue, this being called a "lick". 20 minutes after injection the hamster is observed for 40 min and the number of "licks" are counted. The number of "licks" serves as a quantitative indication of the HCl induced pain.

The analgesic effect is determined by comparing the mean number of "licks" in control animals to the number in treated animals. The significance of the difference was determined using t-test statistics.

B. Lethal Dose Determination

Four different concentrations of the tested substance were injected into the peritoneum of mice weighing 20–25 grams. Eight mice were injected with each concentration. The method of calculating the dose of the tested substance leading to 50% mortality ($LD_{50}$) is as described in Reed, L. J. and Muench, H. (1938) Am. J. Hygiene 27:493. An $LD_{50}$ unit is defined as the amount of tested substance necessary to cause the death of 50% of the injected mice per 20 g body weight (mg/20 g).

C. Toxicity Determinations

Hamsters were used for short-term determinations (up to 10 days), in which the tested material was injected into the peritoneum for 10 days. Rats were used for long term determinations during which ointment was topically applied once a day, 6 days a week, over a period of 4 months (100 applications total).

In an immediate-term toxicity determination, mice (20–25 grams) were injected subcutaneously with 0.1 or 0.2 ml. of various undiluted Mono Q fractions.

D. Protein Determination

The amount of proteinaceous material in the fraction of the invention and its concentration in each separation were determined spectroscopically at 280 nm using an ovalbumin standard of a known concentration.

EXAMPLES

I. Purification of the Fraction of the Invention from *Vipera palestinae* Venom

In a typical purification, 50–80 mg of *V. palestinae* venom were dissolved in 20 mM Tris buffer, pH 7.5, at a final concentration of 0.1 g/ml. Following centrifugation and the removal of the precipitate, the supernatant was filtered through a microfilter (40 micron) and 0.1–0.2 ml were applied to a 1×10 cm FPLC Mono Q column (Pharmacia). The A solvent consisted of 20 mM Tris buffer pH 7.5 and the B buffer consisted of 20 mM Tris and 0.5M NaCl. Buffer A was used alone during the first 20 min of elution. During the following 45 min, a mixture of buffers A and B (50%:50%) was used, and for the last 5 min, 100% buffer B was used. The fraction of the invention eluted in the region of 20–25 min (see FIG. 2B), as determined by various assays (see below). The elution can also be carried out using buffer A alone, which may be replaced by 20 mM ammonium acetate pH 6.9. One hundred purifications using the Mono Q column were carried out over a period of 3 years, all giving similar results.

II. Characterization of the Fraction of the Invention from *Vipera palestinae* venom A. The Nature of the Fraction of the Invention In order to determine the nature of the fraction of the invention, 0.1 mg of the fraction of the invention prepared on a Mono Q column were dissolved in the solution buffer. In parallel, pronase E was prepared by dissolving 2.4 mg of pronase E in elution buffer (20 mM Tris-HCl, pH 7.5). Three tubes were prepared, one containing the protease only, a second containing the fraction of the invention only, and a third in which the fraction of the invention was incubated with 5 μl of pronase E (0.17 micrograms). The tubes were incubated for 24 hr at room temperature, and then tested for analgesic activity.

The result was that only tube 2 had analgesic activity. This test was repeated 3 times with identical results. It can therefore be concluded that the fraction of the invention is of a proteinaceous nature or a protein is required for ifs analgesic activity.

B. Purity of the Fraction of the Invention

The 20–25 min. fraction from the Mono Q column (see I above) contained 0.02±0.05 S.D. mg/ml protein, based on 10 separation runs. Each run resulted in a yield of 0.1 mg of the fraction of the invention. This amount correspondents to 0.6% of the total venom protein applied to the column. This indicates the high purity of the fraction of the invention.

III. Analgesic Activity

The analgesic activity of the fraction of the invention was tested using preparations prepared over a period of two years. 0.2 ml of the fraction of the invention fraction containing 0.01 mg protein were dissolved in 50 gr of ointment resulting in a concentration of 0.0002 mg of the fraction of the invention/g ointment. Hamsters were topically treated with the ointment as described in the Methods section for 21 days. The results are summarized in is Table 1.

TABLE 1

| Date of experiment | May 1991 | June 1991 | December 1991 | May 1992 | April 1993 | May 1993 | September 1993 |
|---|---|---|---|---|---|---|---|
| Sample* | 3 ± 3 | 11 ± 15 | 8 ± 7 | 2 ± 4 | 17 ± 22 | 8 ± 5 | 16 ± 11 |
| Control* | 85 ± 29 | 44 ± 11 | 55 ± 28 | 16 ± 9 | 58 ± 45 | 49 ± 42 | 41 ± 34 |
| p | 0.000 | 0.0009 | .0000 | .0009 | 0.0142 | .0008 | 0.028 |

*average number of "licks" from 7 experiments ± S.D.

These experiments show that the hamsters treated with the fraction of the invention had reduced sensation to the HCl induced pain as compared to the control. The fraction of the invention prepared with the Mono Q column is completely separated from the toxic components of the venom, as is discussed below.

IV. Toxicological Studies

A. Injection of the Fraction of the Invention

A1. Mice (20–25 gr each) were injected s.c. with an amount of 0.05 mg of the fraction of the invention prepared using the Mono Q column. This amount is 250 times the amount necessary to produce an analgesic effect in hamsters. At this dose, the fraction of the invention was not toxic to the mice, and no visible symptoms were observed. In contrast injection of 0.02 mg of the first fractions (tubes 2–7) eluted from the column caused immediate death of all 5 mice injected. This finding demonstrates the substantial non-toxicity of the analgesic fraction.

A2. In a further experiment, 3 groups of 8 hamsters (100–120 grams) each were injected with the fraction of the invention. Lyophilized fraction was dissolved in a physiological saline solution at a concentration of 0.002 mg/ml and 0.1 ml or 0.2 ml were injected daily for 10 days into the peritoneum of the first and second groups, respectively. The third (control) group was injected with 0.2 ml of saline only. Following the 10 days of injections, blood was taken for the testing of biochemical parameters and histopathological tests.

Among the biochemical factors tested, an increase in cholesterol and amylase were observed in the first two groups (results not shown). However no significant changes were observed in the function of liver enzymes (LDH, SGOT, SGPT).

A3. The histopathology of the experimental animals of Section A2 was investigated. No significant histopathological differences were detected between the groups injected with the fraction of the invention and the control group.

B. Topical Treatment

The fraction of the invention was prepared in ointment as described in the Methods section (analgesic assay). Three groups of 10 rats each (males and females) in a weight range of 120–140 g were used. The ointment was topically applied as described in the Methods section. The ointment applied to groups 1 and 2 comprised the fraction of the invention at a concentration of 0.0002 and 0.001 mg/g, respectively. In group 3, the ointment comprised solvent alone as a control. 0.2 g of ointment were applied daily to each rat. During the four months of the experiment, each rat of group 1 received a total of 0.03 mg/kg body weight and each rat of group 2 received 0.15 mg/kg body weight. During the experiment, no changes in the rats' behavior or body weight were observed.

Blood and urine were collected in the laboratory. For collecting of urine, the animals were placed on a plastic surface, the urine collected and immediately tested using Multistick. For the taking of blood the rats were anesthetized and arterial blood taken. The plasma was removed by centrifugation, stored at 4° C. and tested for biochemical parameters.

B1. No increase in SGPT or SGOT was detected. No significant differences with the control group were detected in the following blood analyte levels: Cre; $Ca^{2+}$; P(i); Glu; Ur; Chl; TP; Alb; Bili; Al.Phos; AMY (results not shown).

B2. The results of the measurement of various biochemical parameters in urine are summarized in Table 2:

toxylin and Oozin were used for staining. The following tissues were tested: (1) Skin in the area treated; (2) Skin in an untreated area; (3) heart; (4) kidneys; and (5) brain.

The tissues were taken from: (1) Eight out of ten rats treated with 0.0002 mg/g of analgesic fraction; (2) Six out of ten rats treated with 0.001 mg/g of analgesic fraction; and (3) the control of eight rats. All tested rats were chosen randomly.

The results are summarized in Table 3.

TABLE 3

| Tissue | Control | the fraction of the invention (mg/Kg body weight) | |
|---|---|---|---|
| | | (0.03) | (0.15) |
| Skin | decrease of 50–90% in hair roots in all rats | decrease of 50–90% in hair roots in all rats | decrease of 50–90% in hair roots in all rats |
| Heart | no change | no change | no change |
| Liver | in 2 livers, a small and local case of neutrophils; in all other 6 no changes were seen | in one rat a chronic inflammatory site; no changes in others | in one rat a chronic inflammatory site |
| Kidney | no change | in one rat sites of expansion; in others, no change | no change |
| Brain | no change | no change | no change |

The conclusion was that no significant histopathological changes were observed between the treated and control groups.

In summary, the fraction of the invention isolated from *Vipera palestinae* venom was found to have no significant toxicity.

V. Additional Purification of *Vipera palestinae*

Figure 2:
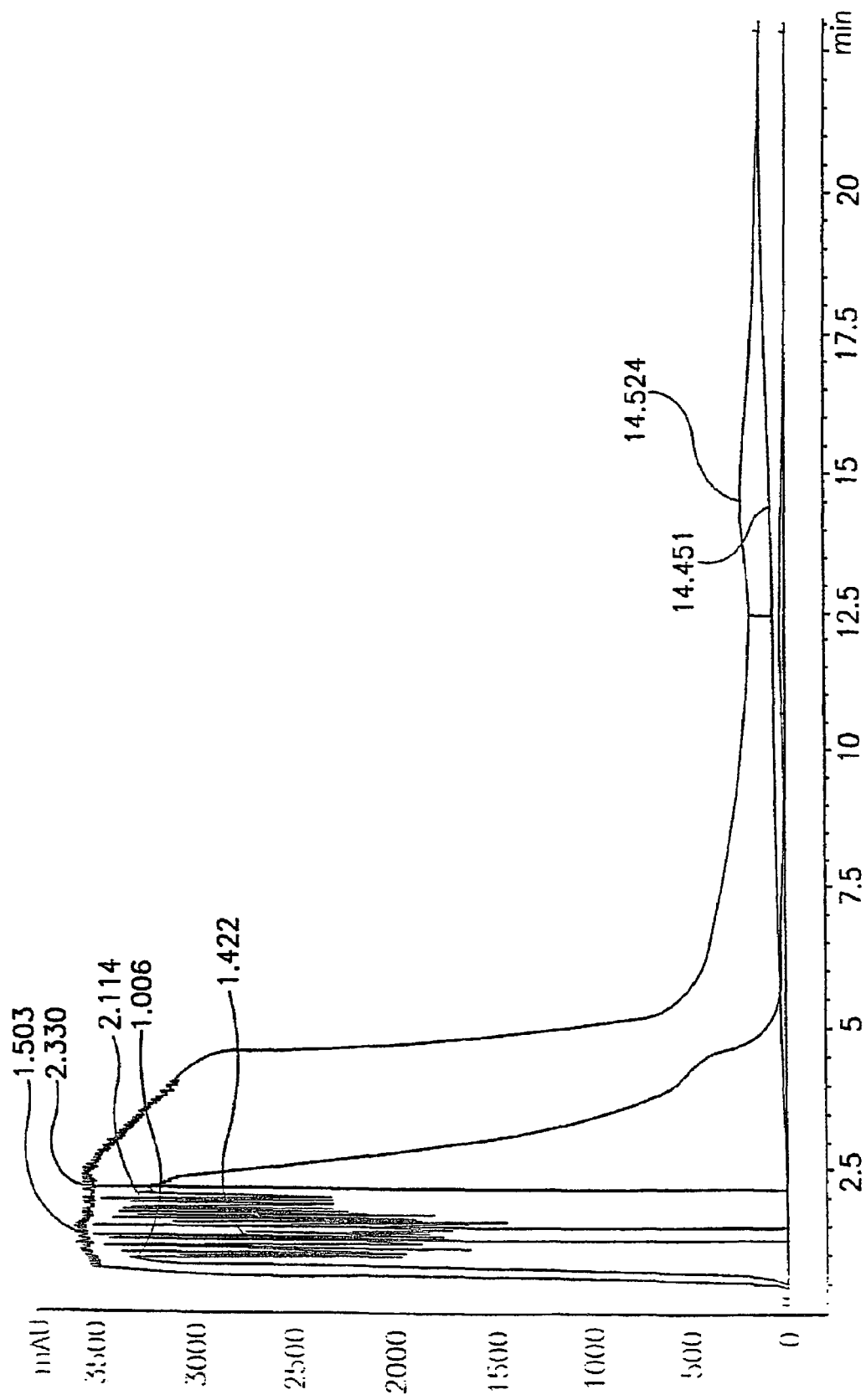
FIG. 2 illustrates the results obtained during another purification of *Vipera palestinae* venom on a Mono Q column.

In additional purifications of *Vipera palestinae* venom on the Mono Q column using 20 mM Tris-HCl buffer, pH 7.0, without NaCl, the fraction of the invention eluted at 13–17 minutes with a peak at 14.5 minutes (FIG. 2).

TABLE 2

| | Glucose | Biliriubin | Ketone | Specific Activity | Blood Non-Hemolyzed | pH | Protein | Uro-binogen | Nitrate | Leukocytes |
|---|---|---|---|---|---|---|---|---|---|---|
| Control (8 rat) | (−) | (+) 1 | (−) | 1.014 | (0) 1 | 7.6 | (0) 2 (−) 6 | 0.2 | (+) 1 (−) 7 | (0) 1 (−) 7 |
| Mono Q Fraction 0.0002 mg/gr (11 rats)* | (−) | (−) | (0) 5 (−) 6 | 1.014 | (0) 2 (−) 9 | 6.9 | (++) 1 (0) 2 (−) 8 | 0.2 | (−) | (−) |

*Only male rats used.
The analyte levels in the table are indicated as follows: (−) negative; (0) traces; (+) low; (++) intermediate. The number following the parenthesis indicates the number of rats tested.

No significant differences were detected.

B3. The histopathology of adult rats treated topically with the fraction of the invention dissolved in ointment was investigated. The day following the last application of ointment, the animals were sacrificed and their skins and tissues were removed and fixed in formalin. Tissues were embedded in paraffin and sliced into 6 micron slices. Hema- VI. Preparation and Characterization of the Fraction of the Invention from *Vipera russelli*

A. Purification

Figure 3:
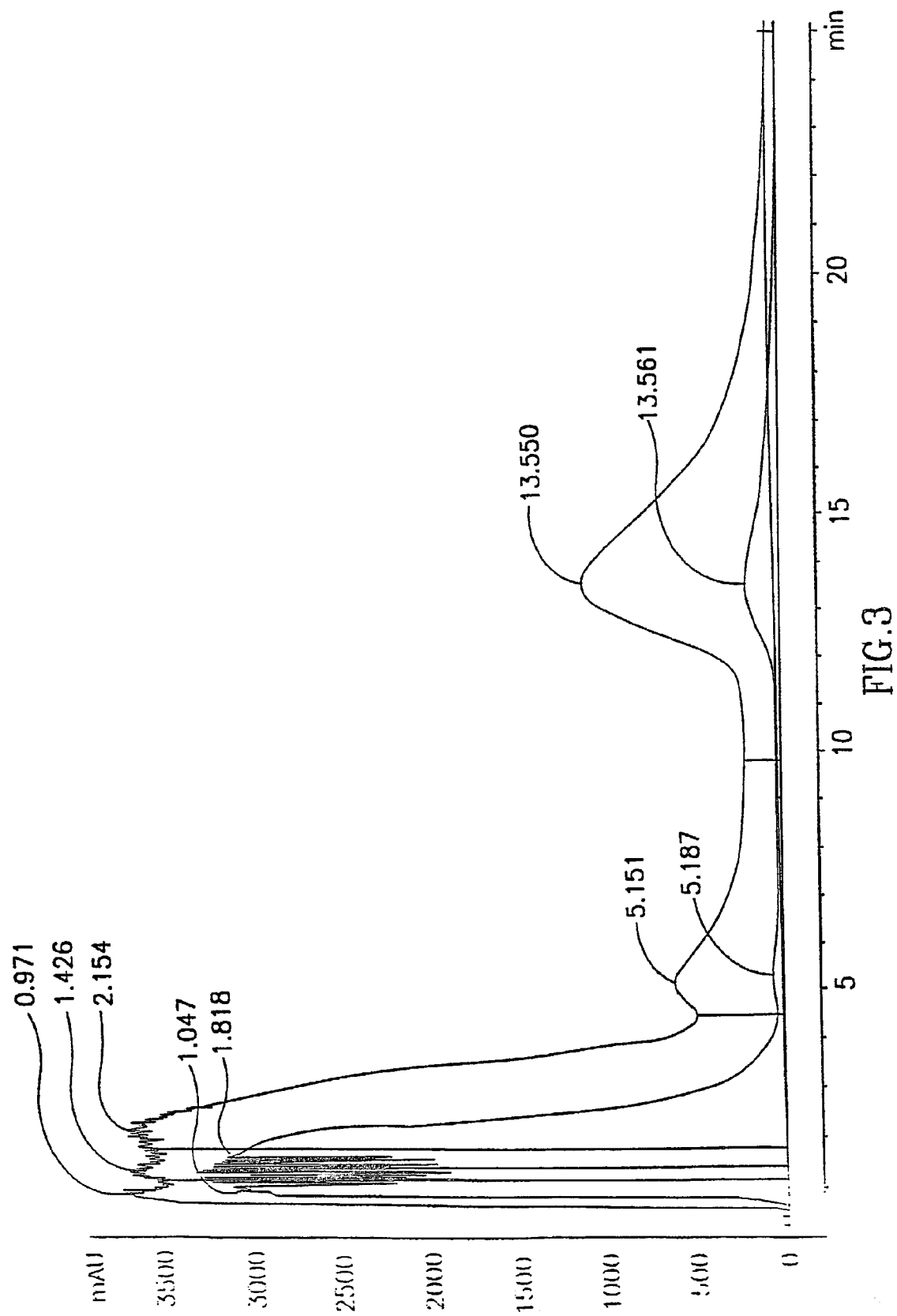
FIG. 3 illustrates the results obtained during a purification of *Vipera russelli* venom on a Mono Q column.

*Vipera russelli* venom was purified on the Mono Q column using 20 mM Tris-HCl buffer, pH 7.0. The fraction of the invention eluted at 12–17 minutes with a peak at 13.5 minutes (FIG. 3).

B. Analgesic Activity

The fraction purified as in VI-A above was tested for analgesic activity in hamsters as described in the Methods section. It was found that whereas the number of licks (average±S.D.) for the control was 83.8±11.8, the number of licks of the treated hamsters was 47.6±7.7 (p<0.02). This indicates that the fraction possesses a significant analgesic activity.

C. Toxicological Studies

Immediate-term toxicity of the Mono Q fractions was measured by subcutaneous injection in mice. It was found that 0.1 ml. of the fractions which eluted at 0.3–4.3 minutes caused immediate death of the mice injected. 02 ml. of the fractions (including the analgesic fractions) eluting after 5 minutes had no toxicity.

VII. Preparation and characterization of the fraction of the invention from *Crotalus adamanteus*.

A. Purification

Figure 4:
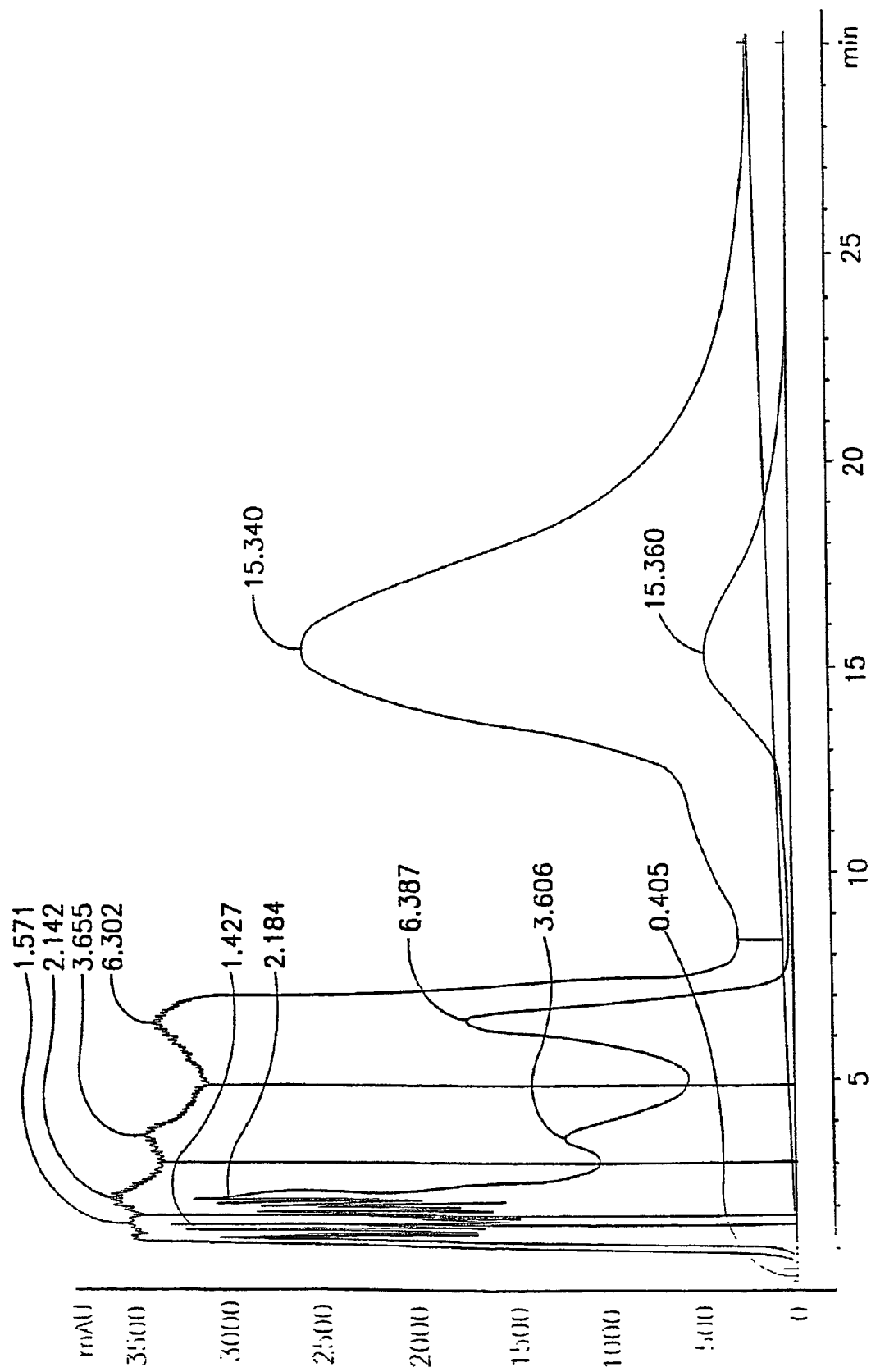
FIG. 4 illustrates the results obtained during a purification of *Crotalus adamanteus* venom on a Mono Q column.

*Crotalus adamanteus* venom was purified on the Mono Q column using 20 mM Tris-HCl buffer, pH 7.0. The fraction of the invention eluted at 10–20 minutes with a peak at 15.3 minutes (FIG. 4). In another purification using 20 mM ammonium acetate buffer, pH 7.0, the fraction eluted at 12.5–17 minutes (results not shown).

B. Analgesic Activity

The fraction purified as in VII-A above was tested for analgesic activity in hamsters as described in the Methods section. It was found that whereas the number of licks (average±S.D.) for the control was 83.8±11.8, the number of licks of the treated hamsters was 25.3±5.3 (p=0.00). This indicates that the fraction possesses a significant analgesic activity.

C. Toxicological Studies

Toxicity of the Mono Q fractions was measured as in VI(c) above. It was found that the toxic fractions eluted at 0.5–5.0 minutes. All of the fractions (including the analgesic fractions) eluting after 5 minutes had no toxicity.

VIII. Preparation and Characterization of the Fraction of the Invention from *Naja melanoleuca*.

A. Purification

Figure 5:
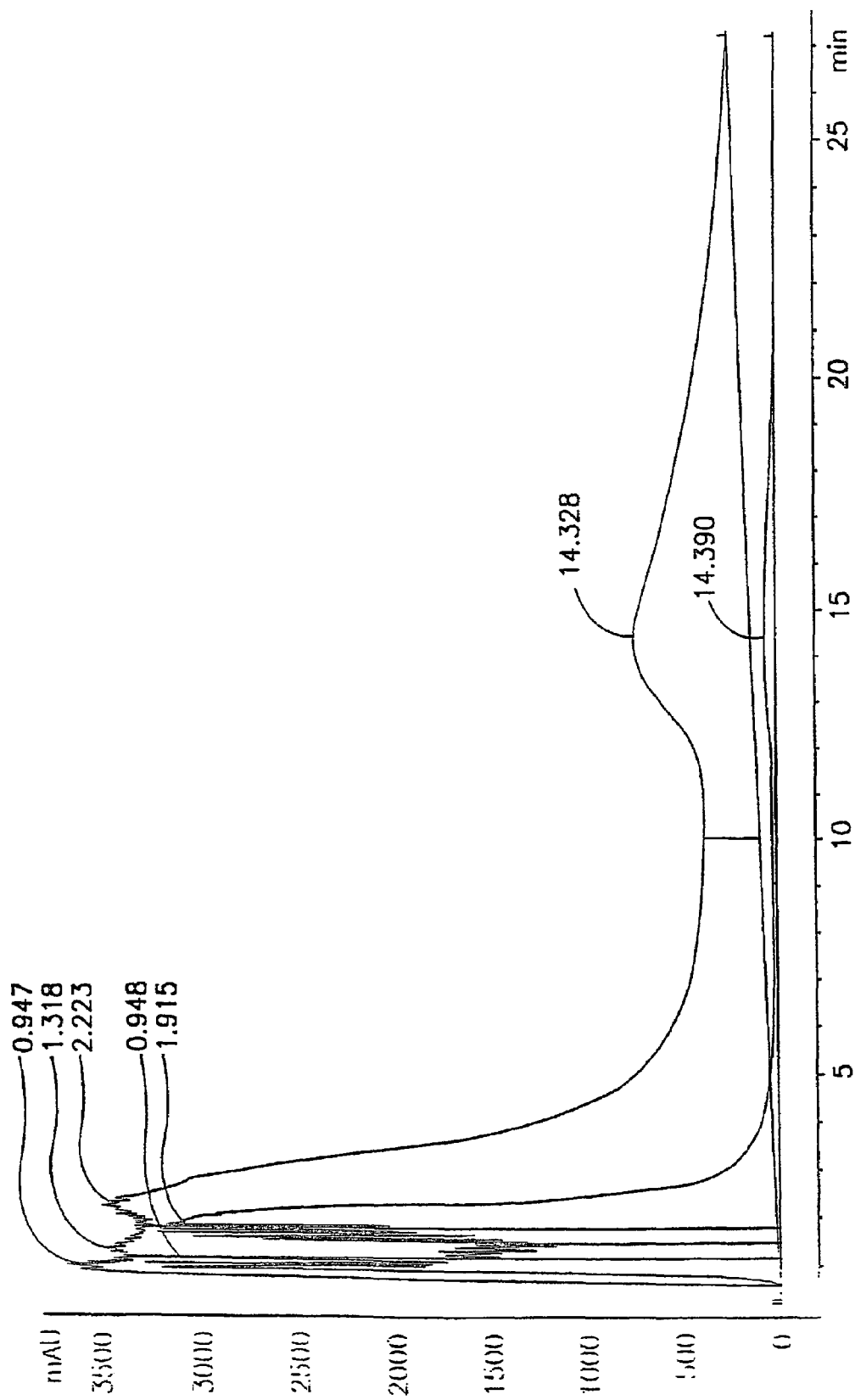
Figure 6:
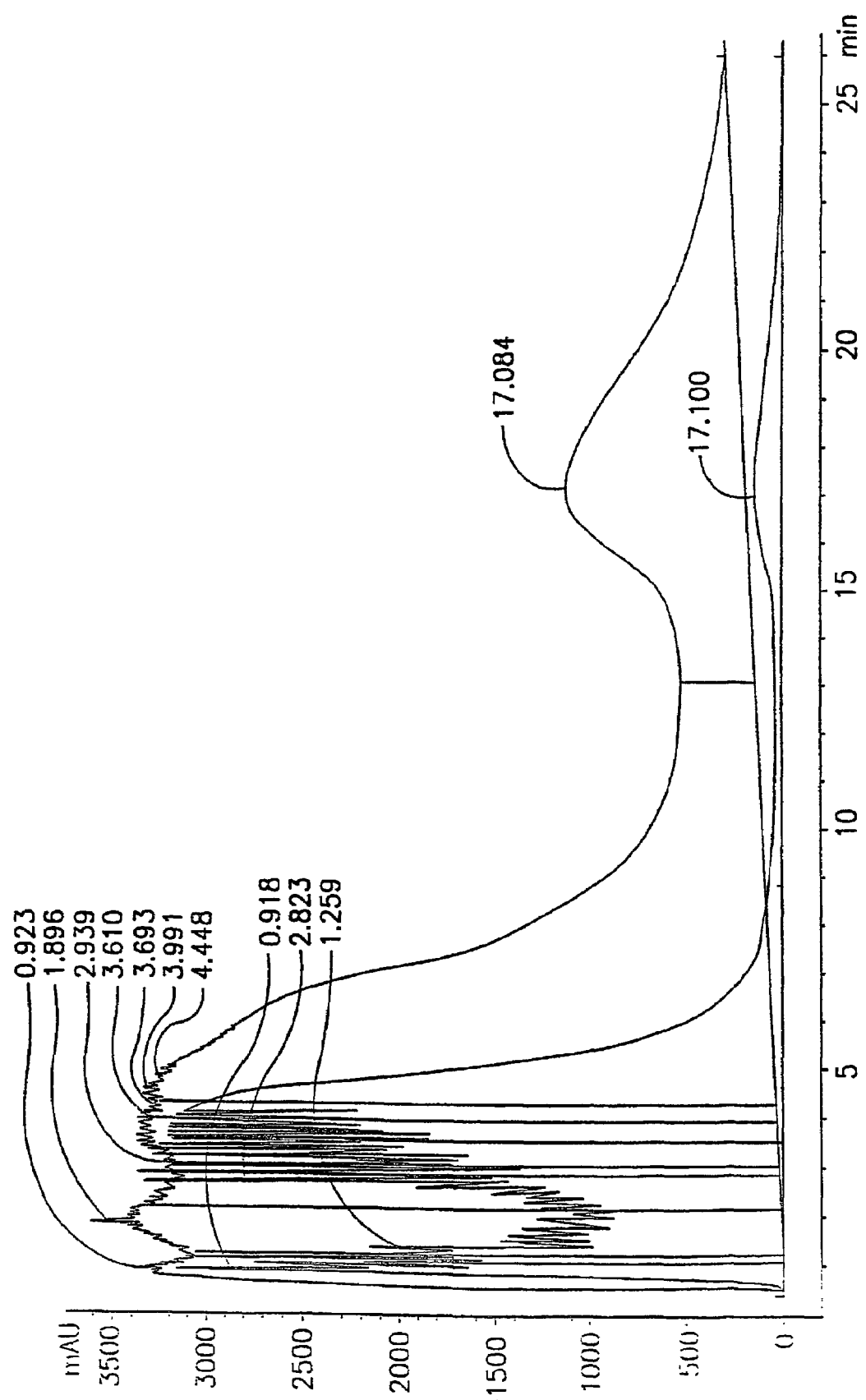
FIG. 6 illustrates the results obtained during a purification of *Naja melanoleuca* venom on a Mono Q column using ammonium acetate buffer.

*Naja melanoleuca* venom was purified on the Mono Q column using 20 mM Tris-HCl buffer, pH 7.0. The fraction of the invention eluted at 12–18 minutes with a peak at 14.3 minutes (FIG. 5). In another purification, the venom was purified using 20 mM ammonium acetate buffer, pH 6.9. The fraction eluted with a peak at 17 minutes (FIG. 6).

B. Toxicological Studies

Toxicity of the Mono Q fractions was measured as in VI(c) above. It was found that the toxic fractions eluted at 0.1–4.0 minutes. All of the fractions (including the fraction of the invention) eluting after 5 minutes had no toxicity.

It will be appreciated by persons skilled in the art that the present invention is not limited to what has been thus far described, but rather the scope of the present invention is limited only by the following claims.

The invention claimed is:

1. A substantially non-toxic analgesic fraction isolated from snake venom, the substantially non-toxic analgesic fraction having an analgesic effect after a lag period, and the snake is selected from the group of snake families consisting of Atractaspidae, Elapidae, Crotalidae, Hydrophidae and Viperidae, with the exception of *Vipera Xanthina*, wherein the substantially non-toxic analgesic fraction has the characteristics of a fraction purified from snake venom by FPLC Mono Q ion-exchange chromatography carried out using an eluent comprising a mixture of 20 mM Tris-HCL buffer pH 7.0 and 20 mM Tris/0.5 M NaCl buffer, where the substantially non-toxic analgesic fraction elutes at 12–28 minutes during an elution period of 45 minutes.

2. The substantially non-toxic analgesic fraction according to claim 1 wherein said Crotalidae is *Crotalus adamanteus*.

3. The substantially non-toxic analgesic fraction according to claim 1 wherein said Elapidae is *Naja melanoleuca*.

4. A product obtained from the substantially non-toxic analgesic fraction of claim 1 which retains said properties of the fraction.

5. A pharmaceutical composition for use as an analgesic comprising a substantially non-toxic analgesic fraction according to claim 1 and a pharmaceutically acceptable carrier or excipient.

6. The pharmaceutical composition according to claim 5 for topical administration.

7. The pharmaceutical composition according to claim 5 for parenteral administration.

8. The pharmaceutical composition according to claim 5 for the treatment of pain.

9. A method for relieving pain in a subject comprising administrating to said subject a substantially non-toxic analgesic fraction according to claim 1.

10. The method according to claim 9 wherein the substantially non-toxic analgesic fraction is topically administered.

11. A method for isolating a substantially non-toxic analgesic fraction from snake venom, comprising applying whole venom to an ion exchange column and eluting the substantially non-toxic analgesic fraction having an analgesic effect with an aqueous buffer, wherein the snake is selected from the group of snake families consisting of Atractaspidae, Elapidae, Crotalidae, Hydrophidae and Viperidae, with the exception of *Vipera Xanthina*, and wherein the substantially non-toxic analgesic fraction has the characteristics of a fraction purified from snake venom by FPLC Mono Q ion-exchange chromatography carried out using an eluent comprising a mixture of 20 mM Tris-HCL buffer pH 7.0 and 20 mM Tris/0.5 M NaCl buffer, where the substantially non-toxic analgesic fraction elutes at 12–28 minutes during an elution period of 45 minutes.

12. The method of claim 11, wherein the ion exchange column is a Mono Q ion-exchange column.

13. The method of claim 12 wherein the Mono Q ion-exchange column is eluted with a TRIS-HCl buffer or with an ammonium acetate buffer.

14. The method according to claim 13 wherein the concentration of the buffer is 20 mM and the pH is in the range of 6.8–7.5.

* * * * *